(12) United States Patent
Stout et al.

(10) Patent No.: US 8,574,255 B2
(45) Date of Patent: Nov. 5, 2013

(54) NARROW-PROFILE LANCING DEVICE

(75) Inventors: Jeffrey T. Stout, Smyrna, GA (US); Avi M. Robbins, Augusta, GA (US); David R. Buenger, Roswell, GA (US)

(73) Assignee: Facet Technologies, LLC, Kennesaw, GA (US)

(*) Notice: Subject to any disclaimer, the term of this patent is extended or adjusted under 35 U.S.C. 154(b) by 453 days.

(21) Appl. No.: 12/715,733

(22) Filed: Mar. 2, 2010

(65) Prior Publication Data

US 2010/0160831 A1 Jun. 24, 2010

Related U.S. Application Data

(62) Division of application No. 11/397,058, filed on Apr. 4, 2006, now abandoned.

(60) Provisional application No. 60/667,958, filed on Apr. 4, 2005.

(51) Int. Cl.
*A61B 17/14* (2006.01)
*A61B 17/32* (2006.01)

(52) U.S. Cl.
USPC .......................................... 606/181; 600/583

(58) Field of Classification Search
USPC .............. 606/181, 182; 600/583, 573; 604/22, 604/110, 117, 207–211; 205/205, 367
See application file for complete search history.

(56) References Cited

U.S. PATENT DOCUMENTS

| 4,577,630 A | 3/1986 | Nitzche et al. |
| 4,637,403 A | 1/1987 | Garcia et al. |
| 4,924,879 A | 5/1990 | O'Brien |
| 5,206,147 A | 4/1993 | Hoenes |
| 5,240,860 A | 8/1993 | Hoenes et al. |
| 5,269,799 A | 12/1993 | Daniel |
| 5,279,294 A * | 1/1994 | Anderson et al. ............. 600/322 |
| 5,334,508 A | 8/1994 | Hoenes |
| 5,382,523 A | 1/1995 | Hoenes et al. |
| 5,463,467 A | 10/1995 | Baumann et al. |
| 5,510,266 A | 4/1996 | Bonner et al. |
| 5,521,060 A | 5/1996 | Hoenes et al. |
| 5,554,166 A | 9/1996 | Lange et al. |
| 5,575,403 A | 11/1996 | Charlton et al. |
| 5,630,986 A | 5/1997 | Charlton et al. |
| 5,720,924 A | 2/1998 | Eikmeier et al. |
| 5,738,244 A | 4/1998 | Charlton et al. |
| RE35,803 E | 5/1998 | Lange et al. |

(Continued)

FOREIGN PATENT DOCUMENTS

| EP | 0894471 A2 | 2/1999 |
| EP | 1230895 A1 | 8/2002 |

*Primary Examiner* — Ryan Severson
*Assistant Examiner* — Katherine M Shi
(74) *Attorney, Agent, or Firm* — Gardner Groff Greenwald & Villanueva, PC

(57) ABSTRACT

In combination, a blood glucose testing meter comprising a slot for receiving a test strip, a display, one or more control devices, and a battery compartment and a lancing device for releasable coupling to the blood glucose test meter over the battery compartment. The lancing device releasably couples directly to the testing meter over the battery compartment. Optionally, the lancing device is mounted to a mounting clip releasably coupled to the testing meter over the battery compartment. The lancing device comprises a housing, a lancet opening disposed at one end of the housing, an energizing member for charging the lancing device, and a release button for activating a lancet within the lancing device.

24 Claims, 17 Drawing Sheets

(56) References Cited

U.S. PATENT DOCUMENTS

| | | |
|---|---|---|
| 5,782,852 A | 7/1998 | Foggia et al. |
| 5,810,199 A | 9/1998 | Charlton et al. |
| 5,854,074 A | 12/1998 | Charlton et al. |
| 5,863,800 A | 1/1999 | Eikmeier et al. |
| 6,022,366 A | 2/2000 | Schraga |
| 6,036,919 A | 3/2000 | Thym et al. |
| 6,045,567 A | 4/2000 | Taylor et al. |
| 6,156,051 A | 12/2000 | Schraga |
| 6,192,891 B1 | 2/2001 | Gravel et al. |
| 6,197,040 B1 | 3/2001 | LeVaughn et al. |
| 6,207,000 B1 | 3/2001 | Schwobel et al. |
| D448,294 S | 9/2001 | Alscher et al. |
| 6,302,855 B1 | 10/2001 | Lav et al. |
| 6,322,575 B1 | 11/2001 | Schraga |
| 6,379,317 B1 | 4/2002 | Kintzig et al. |
| 6,409,740 B1 | 6/2002 | Kuhr et al. |
| 6,419,661 B1 | 7/2002 | Kuhr et al. |
| 6,455,001 B1 | 9/2002 | Knappe et al. |
| 6,464,649 B1 | 10/2002 | Duchon et al. |
| 6,475,436 B1 | 11/2002 | Schabbach et al. |
| 6,497,845 B1 | 12/2002 | Sacherer |
| 6,602,268 B2 | 8/2003 | Kuhr et al. |
| 6,613,570 B2 | 9/2003 | Knappe et al. |
| 6,696,024 B1 | 2/2004 | Leichner et al. |
| D487,594 S | 3/2004 | Alscher et al. |
| 6,707,554 B1 | 3/2004 | Miltner et al. |
| 6,749,618 B2 | 6/2004 | LeVaughn et al. |
| 6,811,557 B2 | 11/2004 | Schraga |
| 6,881,378 B1 | 4/2005 | Zimmer et al. |
| 6,887,253 B2 | 5/2005 | Schraga |
| 6,922,576 B2 | 7/2005 | Raskas |
| 6,945,982 B2 | 9/2005 | Marshall et al. |
| 7,008,799 B1 | 3/2006 | Zimmer et al. |
| 7,025,836 B1 | 4/2006 | Zimmer et al. |
| 7,077,828 B2 | 7/2006 | Kuhr et al. |
| 7,105,006 B2 | 9/2006 | Schraga |
| D530,424 S | 10/2006 | Manser et al. |
| 7,175,641 B1 | 2/2007 | Schraga |
| 7,192,405 B2 | 3/2007 | DeNuzzio et al. |
| 7,223,267 B2 | 5/2007 | Isola et al. |
| 7,273,484 B2 | 9/2007 | Thoes et al. |
| 7,311,718 B2 | 12/2007 | Schraga |
| D567,944 S | 4/2008 | Sarna |
| 7,479,118 B2 | 1/2009 | Chan |
| 7,481,777 B2 | 1/2009 | Chan et al. |
| 7,510,564 B2 | 3/2009 | Mace |
| 7,572,269 B2 | 8/2009 | Marshall et al. |
| 7,670,301 B2 | 3/2010 | Roe |
| 7,678,126 B2 | 3/2010 | Schraga |
| 7,708,702 B2 | 5/2010 | Chan |
| 7,727,168 B2 | 6/2010 | Douglas et al. |
| 7,731,668 B2 | 6/2010 | Douglas et al. |
| 2003/0088261 A1 | 5/2003 | Schraga |
| 2004/0215224 A1 | 10/2004 | Sakata et al. |
| 2005/0234495 A1 | 10/2005 | Schraga |
| 2005/0240119 A1 | 10/2005 | Draudt et al. |
| 2005/0288699 A1 | 12/2005 | Schraga |
| 2006/0079920 A1 | 4/2006 | Schraga |
| 2006/0106411 A1 | 5/2006 | Schraga |
| 2006/0157362 A1 | 7/2006 | Schraga |
| 2006/0173478 A1 | 8/2006 | Schraga |
| 2006/0241668 A1 | 10/2006 | Schraga |
| 2006/0241669 A1 | 10/2006 | Stout et al. |
| 2006/0247671 A1 | 11/2006 | LeVaughn |
| 2006/0271084 A1 | 11/2006 | Schraga |
| 2007/0083222 A1 | 4/2007 | Schraga |
| 2007/0185515 A1 | 8/2007 | Stout |
| 2007/0288047 A1 | 12/2007 | Thoes et al. |
| 2008/0045992 A1 | 2/2008 | Schraga |
| 2008/0058847 A1 | 3/2008 | Abe et al. |
| 2008/0082116 A1 | 4/2008 | Lathrop et al. |
| 2008/0147108 A1 | 6/2008 | Kennedy |
| 2008/0167673 A1 | 7/2008 | Zhong et al. |
| 2008/0195132 A1 | 8/2008 | Schraga |
| 2008/0195133 A1 | 8/2008 | Zhong et al. |
| 2008/0200887 A1 | 8/2008 | Haar et al. |
| 2008/0243159 A1 | 10/2008 | Schraga |
| 2008/0262386 A1 | 10/2008 | Haar et al. |
| 2008/0267822 A1 | 10/2008 | List et al. |

* cited by examiner

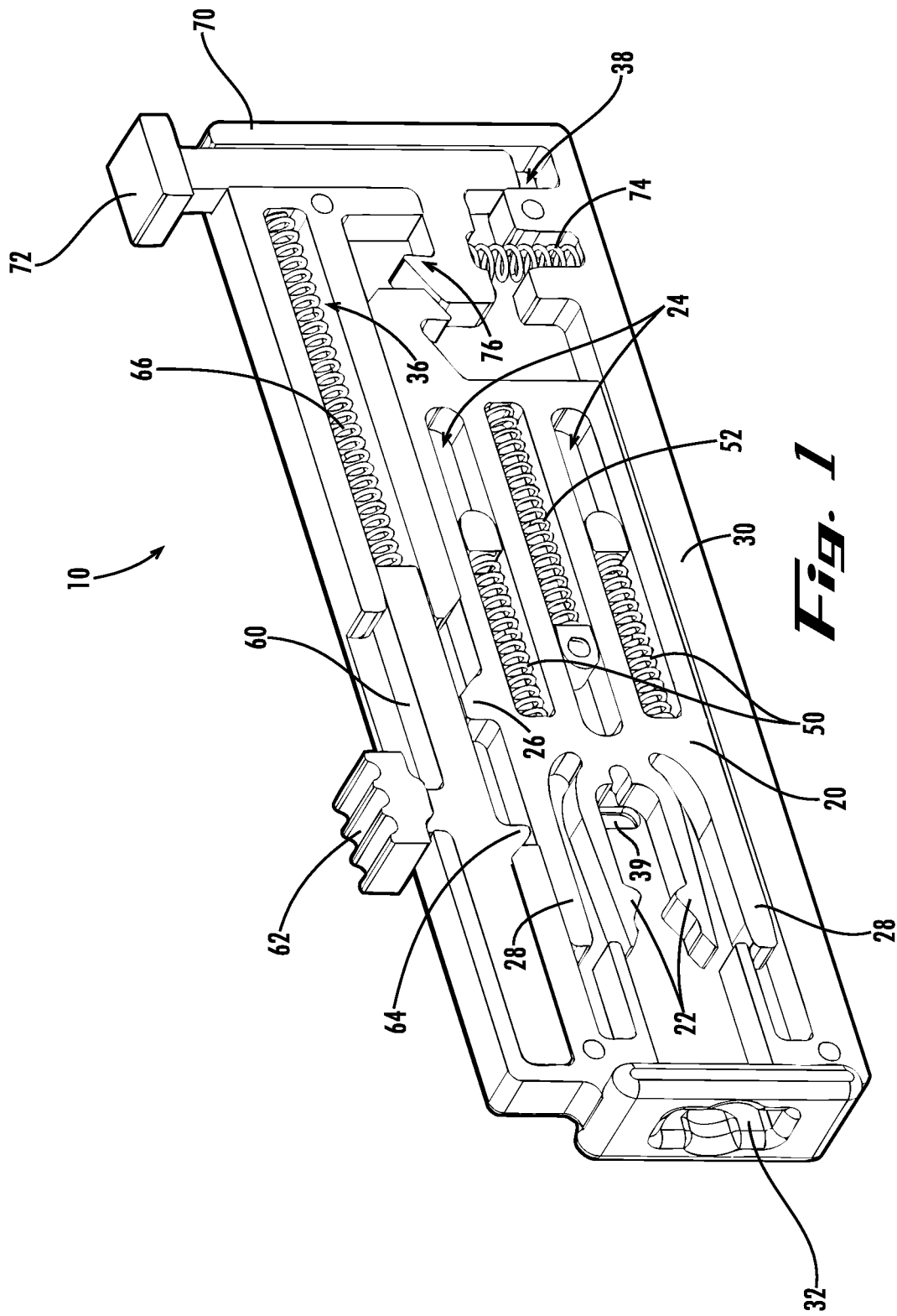

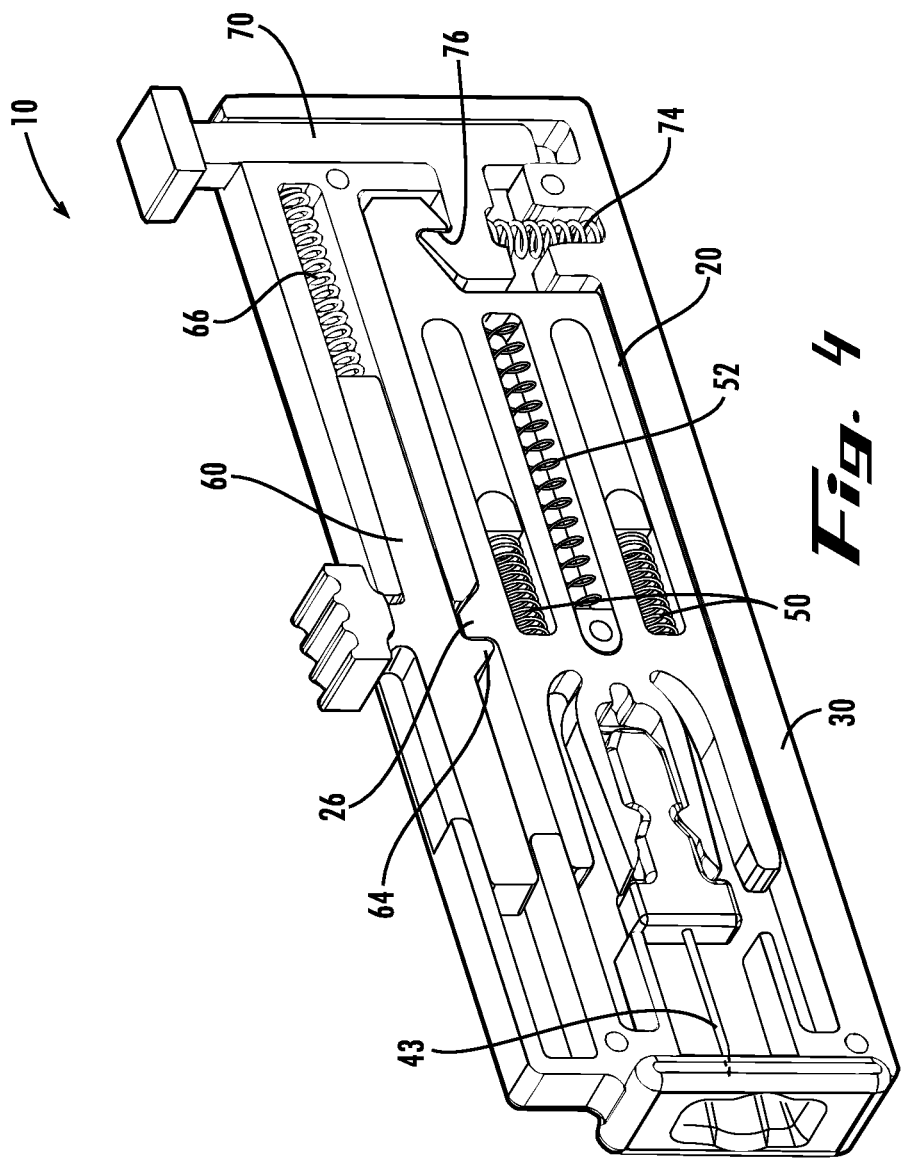

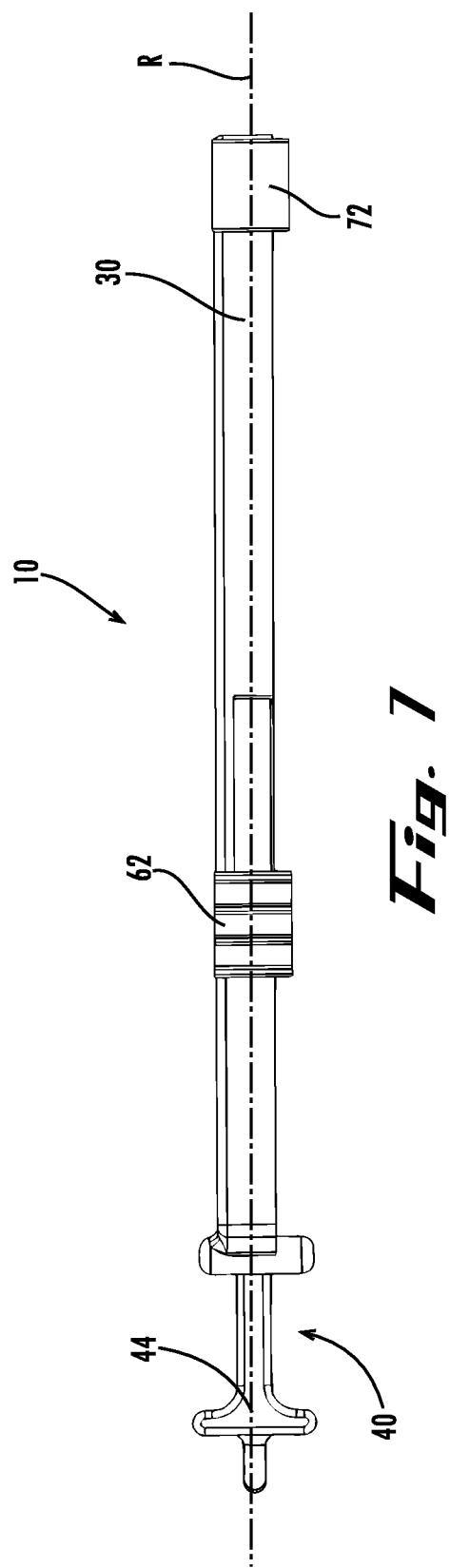

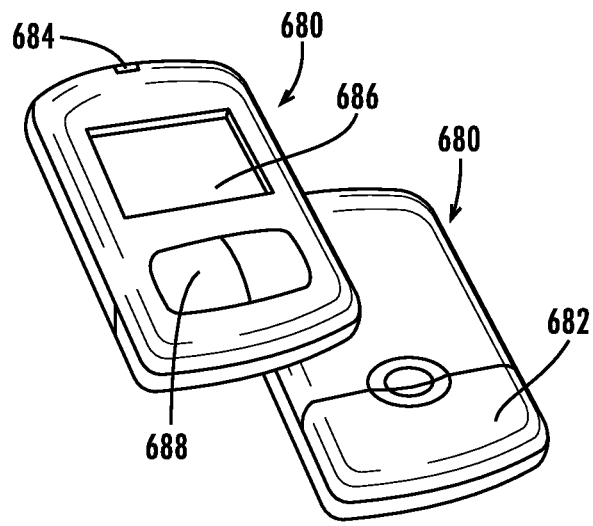
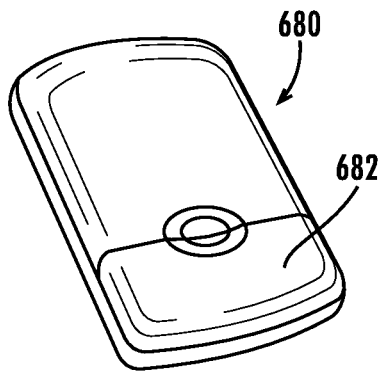
*Fig. 13a*  *Fig. 13b*
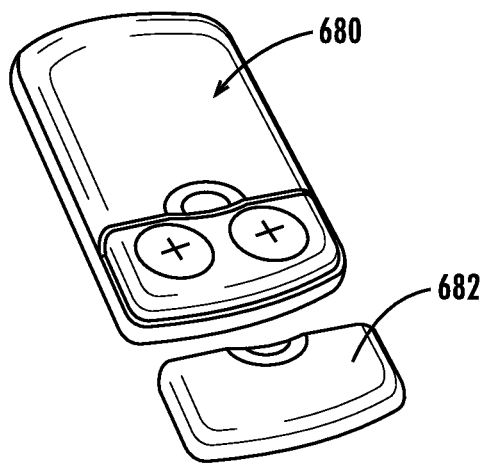
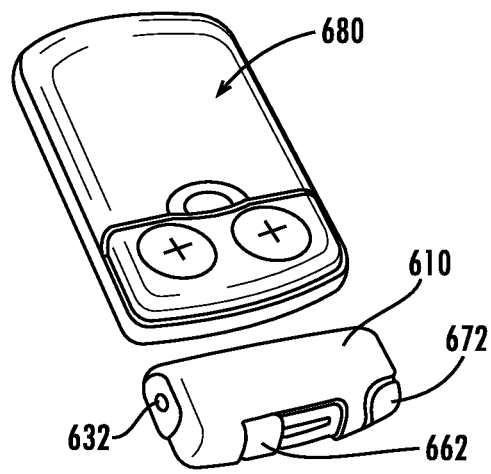
*Fig. 13c*  *Fig. 13d*
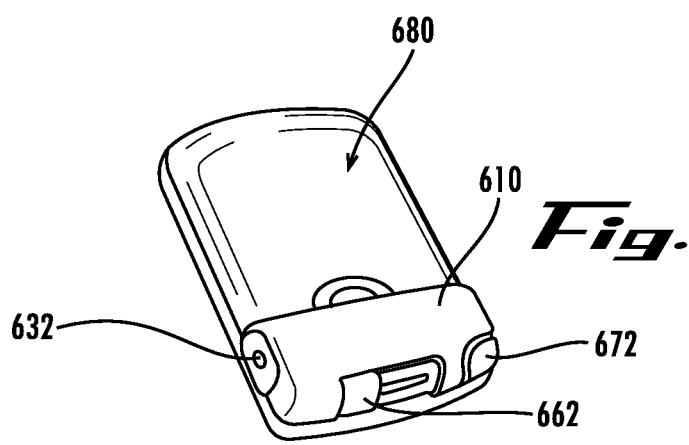
*Fig. 13e*

1

NARROW-PROFILE LANCING DEVICE

CROSS-REFERENCE TO RELATED APPLICATION

This application is a divisional of U.S. Non-Provisional patent application Ser. No. 11/397,058, filed Apr. 4, 2006, which claims the benefit of U.S. Provisional Patent Application Ser. No. 60/667,958, filed Apr. 4, 2005; which applications are incorporated herein by reference in their entirety for all purposes.

TECHNICAL FIELD

The present invention relates generally to lancing devices for medical sampling of blood or other body fluids of a human or animal subject. More particularly, the invention relates to a miniature lancing device having components arranged in a compact planar configuration allowing the device to have a narrow profile relative to typical lancing devices.

BACKGROUND

Many medical procedures require puncturing of the skin, and sometimes underlying tissues, of an animal or human subject. For example, a sharp lancet tip is commonly used to puncture the subject's skin at a lancing site to obtain a sample of blood or other body fluid, as for example in blood glucose monitoring by diabetics and in blood typing and screening applications. A lancing device having a spring-loaded or otherwise energized drive mechanism is often used to carry the lancet along a path of travel, between a retracted or shielded position and an extended position wherein the lancet tip punctures the skin.

Various forms of lancing devices are known. Many users, however, have found known lancing devices to be too bulky and inconvenient to carry and stow in a pocket or bag. Also, some users find it inconvenient to carry multiple separate components for sampling and testing, such as a lancing device and a meter. Perceived inconvenience can lead to non-compliance with a prescribed testing regimen, potentially adversely affecting the subject's health.

Thus it can be seen that needs exist for improvements to lancing devices to provide a smaller and thinner lancing device. Needs further exist for a lancing device that can be attached to a blood glucose meter for convenience and to avoid loss. It is to the provision of an improved lancing device meeting these and other needs that the present invention is primarily directed.

SUMMARY

In example forms, the present invention relates to a miniature lancing device having a thin profile, for easy and convenient stowage. Optionally, the lancing device is configured to be provided as an original component of, or to be attached as a retrofit component onto a glucose test meter. For example, an example embodiment of the invention is a miniature lancing device configured to be used in place of a battery compartment cover of a glucose test meter. This allows the device to be retrofitted on existing meters, or provided as original equipment on a new meter, thereby providing an integrated device.

In a first aspect, the invention relates to a combination of a body fluid testing meter having a battery cover opening, and a lancing device configured for engagement with the meter over the battery cover opening. The lancing device releasably couples directly to the body fluid testing meter over the battery compartment. The lancing device includes a housing and a lancet opening disposed at one end of the housing. The lancet opening of the lancing device projects beyond or is adjacent to an outer peripheral edge of the testing meter. The housing of the lancing device comprises external surface features substantially conforming to attachment clips, channels, tabs, slots, and/or other corresponding coupling members of a battery cover of the testing meter. Optionally, the lancing device is used in place of a battery cover of the testing meter to cover the battery compartment and the lancing device generally matches the shape and size of the battery cover.

In another aspect, the invention relates to a combination of a body fluid testing meter and a lancing device is mounted to a mounting clip releasably coupled to the blood glucose test meter over the battery compartment. The lancing device comprises a housing, a lancet opening disposed at one end of the housing, an energizing member for charging the lancing device, and a release button for activating a lancet within the lancing device.

These and other aspects, features and advantages of the invention will be understood with reference to the drawing figures and detailed description herein, and will be realized by means of the various elements and combinations particularly pointed out in the appended claims. It is to be understood that both the foregoing general description and the following brief description of the drawings and detailed description of the invention are exemplary and explanatory of preferred embodiments of the invention, and are not restrictive of the invention, as claimed.

BRIEF DESCRIPTION OF THE DRAWINGS

FIG. 3 shows the lancing device of FIG. 1 with the lancet engaged in the drive mechanism.

FIG. 4 shows the lancing device of FIG. 1 with the drive mechanism charged and the endcap of the lancet removed to expose the sharp lancet tip.

FIG. 7 is a top view of the lancing device of FIG. 1 showing its narrow profile.

FIGS. 13a-13e show a lancing device according to another embodiment of the present invention, the lancing device being installed in place of a battery cover on a blood-glucose testing meter.

DETAILED DESCRIPTION OF EXAMPLE EMBODIMENTS

Figure 2:
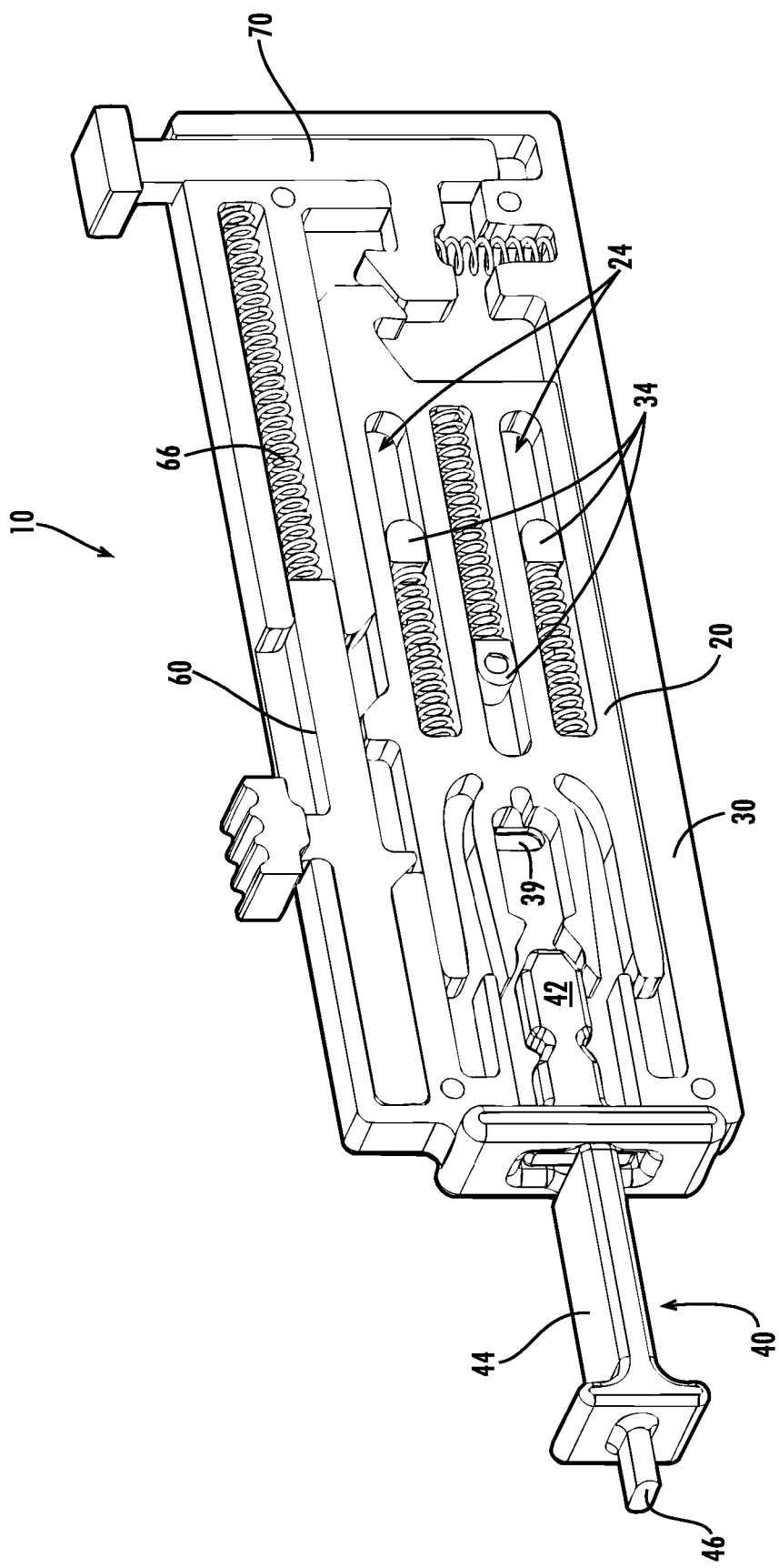
FIG. 2 shows the lancing device of FIG. 1 with its drive mechanism in an equilibrium position and receiving a lancet.
Figure 1:
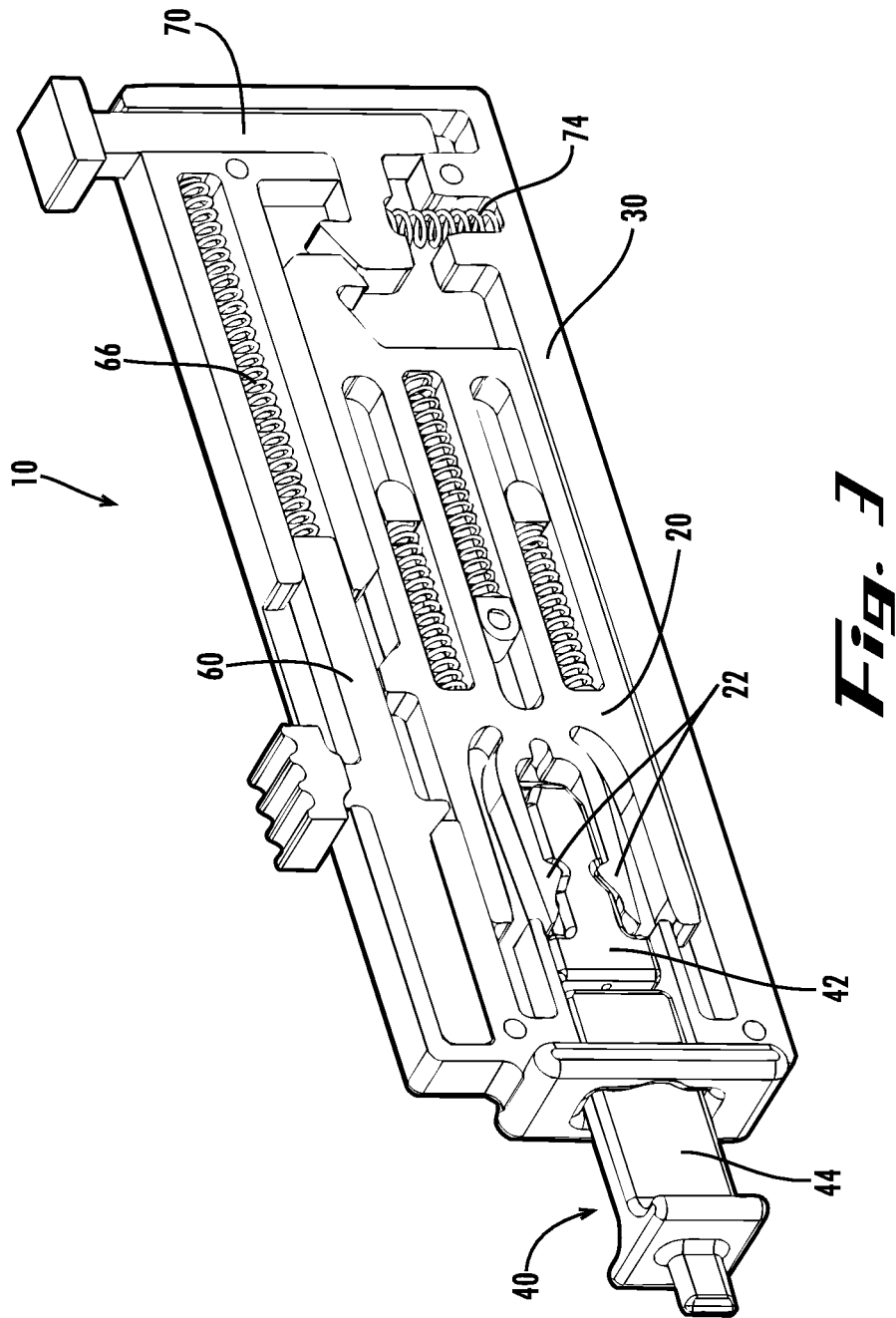
FIG. 1 is a perspective view of a lancing device according to an example form of the present invention, with an outer cover portion removed to show internal components thereof.

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

With reference to FIGS. 1-7, an example form of a lancing device 10 according to the present invention is shown. A lancet holder or carrier 20 is translationally mounted within a housing 30. The housing 30 is shown in the attached drawing figures with its side cover panels removed to more clearly show internal components. The unshown cover panels are preferably attached by screws, rivets, crush-pins, snap-fittings, adhesive, solvent or thermal welding, or other attachment means to substantially fully enclose the internal components of the device. Alternatively, the housing 30 is an integral component including the unshown side cover portions, for example formed as a single molding of plastic or other structurally stable material(s). The housing 30 preferably has a very compact, flat and slim exterior profile, for example having dimensions of about 0.125" thick×1.85" long×0.725" high (0.3 cm×4.7 cm×1.8 cm) in one example embodiment. In preferred forms, the aspect ratio (height: thickness) of the device is at least 4:1, and more preferably at least 5:1. It is preferred that the overall thickness of the device be less than 0.25" (0.6 cm), and more preferably less than 0.125" (0.3 cm). The compact size and thin profile of the internal componentry of the lancing device of the present invention advantageously permit the device to be used as a standard or generic "core" or chassis platform for various different lancing device formats (i.e., lancing devices having distinct external appearances and geometries may have common internal workings in the form of the device described herein), facilitate easier and more convenient stowage and use, and allow the device to be mounted to a meter or other device without negatively impacting its utility or appearance in a significant manner.

The lancet carrier 20 preferably comprises a pair of resilient fingers or forks 22 for releasably engaging a miniature lancet 40. The lancet 40 is preferably inserted and removed through a slotted opening 32 in the proximal end of the housing 30. The slotted opening 32 has a length considerably greater than its width, most preferably having a length at least twice its width. The lancet carrier 20 preferably also comprises slots 24 and/or contact faces for receiving and/or engaging one or more drive springs 50 and/or one or more retraction springs 52 for advancing and retracting the lancet carrier along its path of travel within the housing 30 to carry the lancet along its lancing stroke. In the depicted embodiment, two drive springs 50 and one retraction spring 52 are included in the form of coil springs, positioned within separate slots extending generally parallel to one another within the carrier 20. In alternate embodiments, a single drive spring is provided, having a substantially greater stiffness than the return spring, and/or torsion springs, leaf springs, or other forms of drive mechanisms are provided. The drive and return springs 50, 52 are preferably captured in compression or otherwise engaged between the contact faces of the lancet carrier 20 and lugs 34 or other surface features, recesses or projections of the housing 30. The walls of the slots and the sidewalls of the housing assist in maintaining the various biasing springs of the lancing device aligned and in place.

An energizing or charging member 60 is preferably translationally mounted to slide within a lengthwise channel 36 in the housing 30, generally parallel to the path of travel of the lancet carrier 20. A gripping pad or surface 62 preferably projects from the energizing member 60, outwardly of the housing, to facilitate actuation by a user. A tooth or pawl 64 projects laterally from the energizing member 60, for engagement with a cooperating projection 26 or other surface feature of the lancet carrier 20. An energizing member return spring 66 is preferably engaged in compression between the energizing member 60 and the housing 30, to bias the energizing member 60 toward the proximal end of the lancing device.

A release member 70 is preferably translationally mounted to slide within a transverse channel 38 in the distal end of the housing 30, generally perpendicular to the path of travel of the lancet carrier 20. The release member 70 preferably includes a release button 72 projecting outwardly from the housing 30 to facilitate user actuation. A release member return spring 74 is preferably engaged in compression between the release member 70 and the housing 30, to bias the release member 70 in the direction of the release button 72. The release member 70 preferably also comprises a sear 76 or other surface feature for releasably engaging a cooperating portion of the lancet carrier 20, to retain the lancet carrier retracted in its energized position until released by the user actuating the release button 72. The lancet carrier 20, the energizing member 60, and the release member 70 are all preferably intersected by a single common reference plane R, are relatively thin in the direction normal to the reference plane, and have generally flat and contiguous side faces lying parallel to the reference plane. Additionally, the associated biasing members 50, 52, 66 and 74 preferably each have their axes of bias along the reference plane R or closely parallel thereto. And the line or path of travel of the lancet 40 preferably also lies in the reference plane R. The thin and planar arrangement of components in this manner allows the overall device 10 to be contained within a very compact and narrow-profile external housing, as seen in example form in FIG. 7.

The lancet 40 of the present invention preferably comprises a small and lightweight lancet body portion 42, preferably having a sharp lancet tip 43 projecting therefrom in the form of a metal needle or blade. Preferably, the lancet body 42 is a molded plastic member having a shank portion of the needle or blade 43 securely embedded therein. The lancet body 42 preferably has a flattened profile along at least a proximal portion of its length, having a first dimension (height) substantially larger than a second dimension (width), and configured to pass freely through the slotted opening 32 in the housing 30 when aligned therewith, but to prevent rotation of the lancet body within the slotted opening of the housing. Notches or recesses in the sides of the lancet body 42 are preferably provided to receive and releasably engage cooperating projections formed on the resilient fingers 22 of the lancet carrier 20. The lancet 40 preferably further comprises a removable sterility cap 44. The sterility cap 44 is preferably co-molded with the lancet body portion 42, and the two are connected at a narrow or notched neck portion for ease of separation upon removal of the sterility cap. The sterility cap 44 is preferably relatively large or oversized, as compared to the lancet body 42, to facilitate easier handling and loading of the lancet into the lancing device, which is of particular advantage to users having reduced visual acuity and/or reduced manual dexterity. The sterility cap 44 optionally has a flared or T-shaped configuration for better gripping during insertion of the lancet and removal of the cap. The sterility cap 44 preferably has a flattened profile along at least a distal portion of its length, generally matching the flattened profile of the proximal portion of the lancet body portion, but initially oriented generally perpendicularly or obliquely relative thereto. The sterility cap 44 preferably also has a release finger 46 projecting therefrom, to assist in release of a used lancet from the fingers or forks of the lancet carrier, as detailed below.

In use, the user loads a lancet 40 into the lancing device 10 by inserting the lancet body 42 into the slotted opening 32 of the housing, until the flattened profile of the lancet's sterility cap 44 contacts the proximal face of the housing 30, with the profile of the sterility cap being oriented generally crosswise to the slotted opening (FIG. 2). The sterility cap 44 is then twisted about 90°, while the lancet body is prevented from twisting due to its flattened profile being engaged within the slotted opening 32, thereby aligning the flattened profile of the cap with the slotted opening. This twisting of the sterility cap 44 serves to sever or detach the sterility cap from the lancet body 42 at the neck portion therebetween, and to loosen the attachment between the sterility cap and the lancet needle. The T-shaped configuration of the sterility cap 44 assists the user in gripping and twisting the cap in this manner. With the profile of the sterility cap 44 now aligned with the slotted opening 32 of the housing, the lancet 40 is inserted further into the housing, until the lancet body 42 snaps into engagement in the resilient fingers 22 of the lancet carrier (FIG. 3). The sterility cap 44 may then be removed, or can be left in place until the device is energized and ready for use.

The user then actuates the energizing member 60 by sliding the gripping pad 62 rearwardly, away from the end of the housing 30 having the slotted opening 32 therein. Engagement of the pawl 64 of the energizing member 60 with the projection 26 of the lancet carrier 20 as the energizing member is operated retracts the lancet carrier and energizes the drive springs 50. Alternatively, pushing the lancet further into the housing energizes the drive spring(s). As the lancet carrier 20 moves into its retracted position, the lancet carrier contacts an inclined surface of the sear 76 of the release member 70, depressing the release member against the bias of the release member return spring 74. Upon reaching its fully retracted position, the sear 76 of the release member 70 snaps upwardly into engagement with the lancet carrier 20 under the influence of the release member return spring 74, to retain the lancet carrier retracted in its energized position (FIG. 4). The user then releases the energizing member 60 to return to its forward position under the influence of the energizing member return spring 66.

Figure 5:
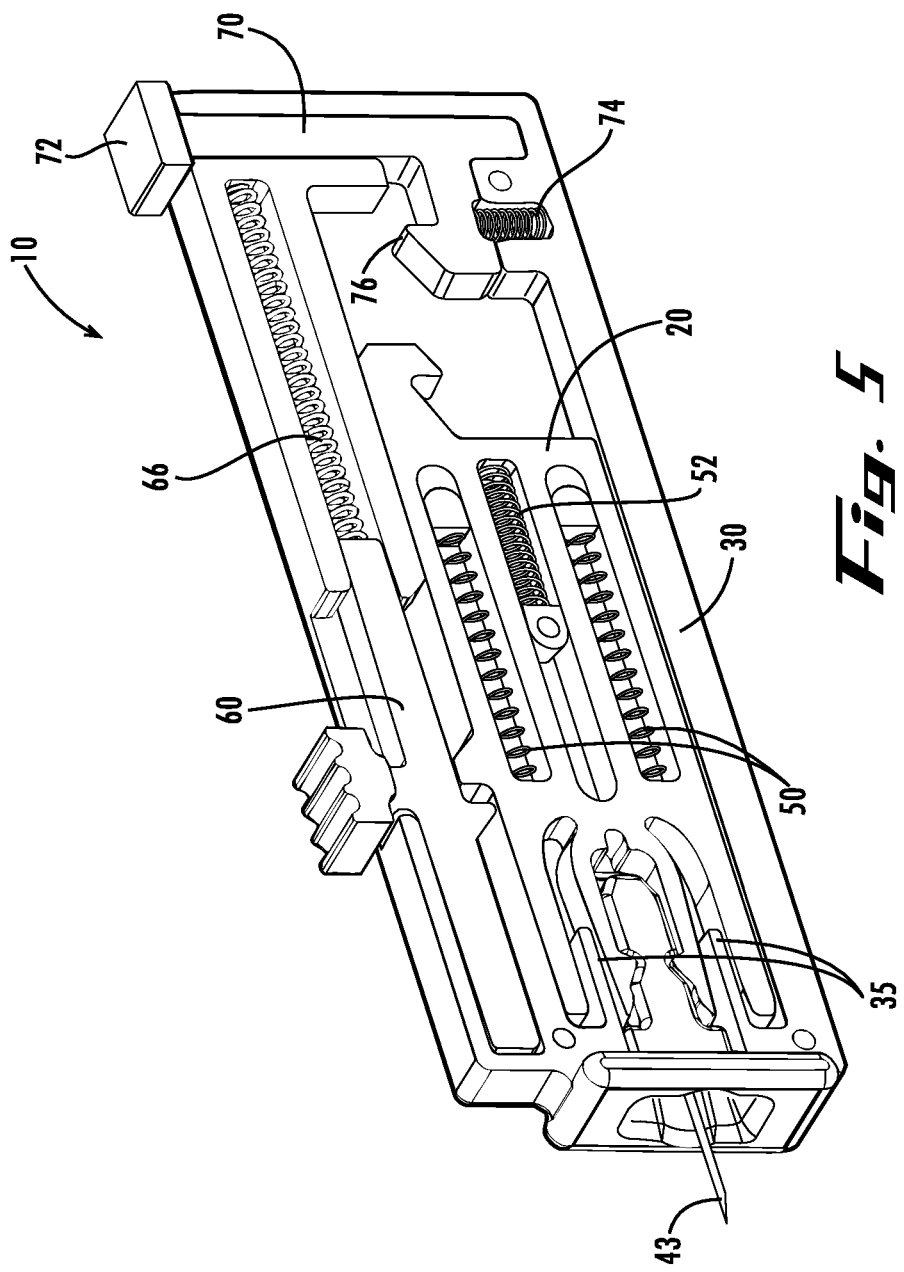
FIG. 5 shows the lancing device of FIG. 1 with its activation mechanism released, the drive mechanism in its forward or lancing position, and the tip of the lancet projecting outwardly from the device's lancet opening.
Figure 6:
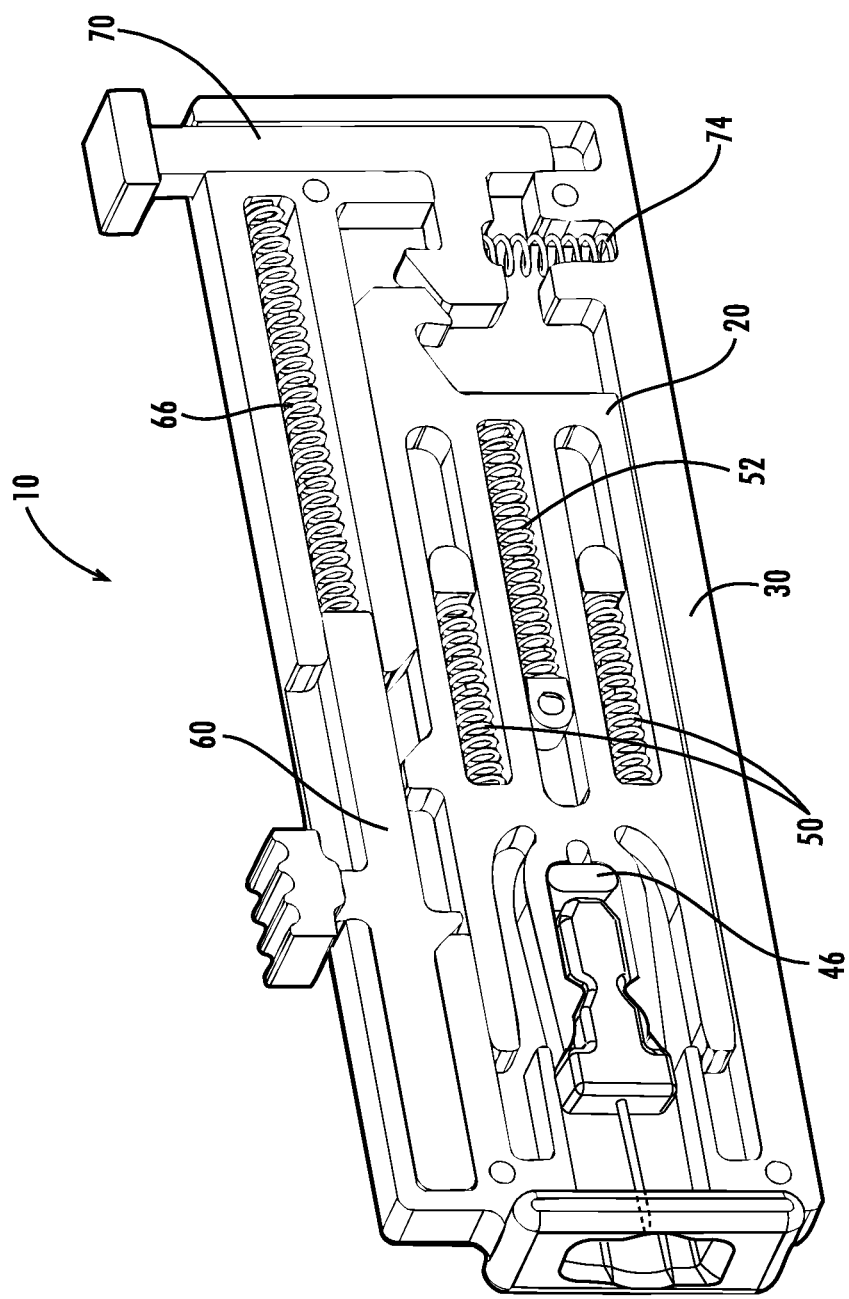
FIG. 6 shows the lancing device of FIG. 1 with the drive mechanism returned to its equilibrium position and the lancet tip retracted back into the device after lancing, and with a release member positioned for lancet removal.
Figure 8A:
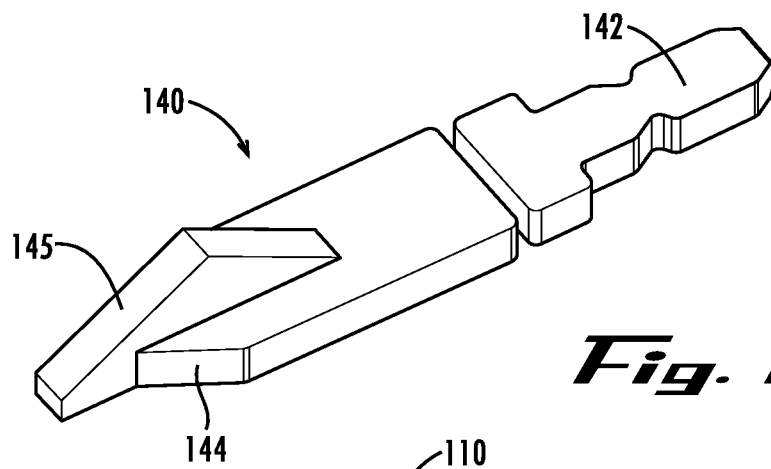
FIGS. 8a-8h show a lancing device and lancet according to another embodiment of the present invention.
Figure 8B:
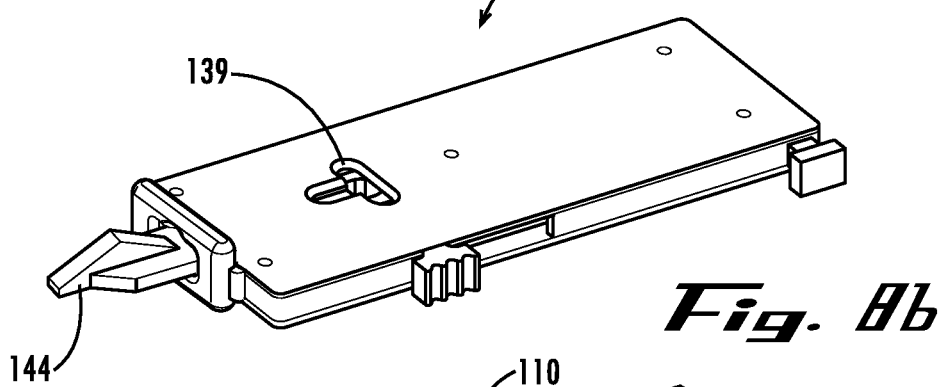
Figure 8C:
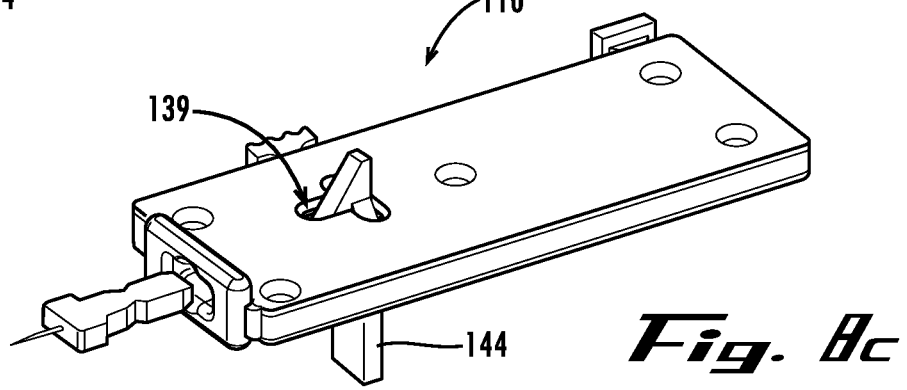
Figure 8D:
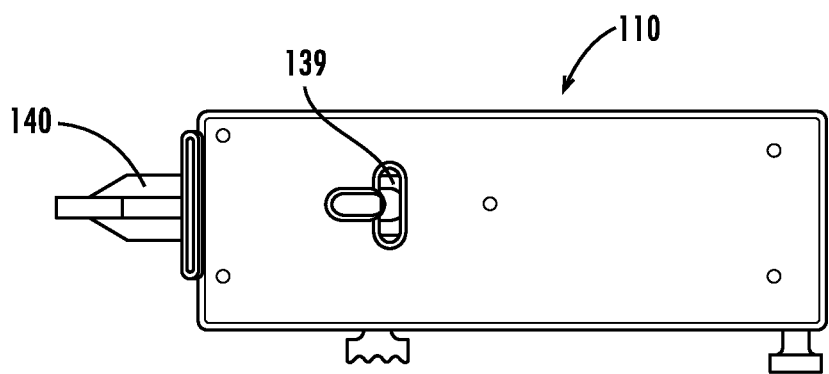
Figure 8E:
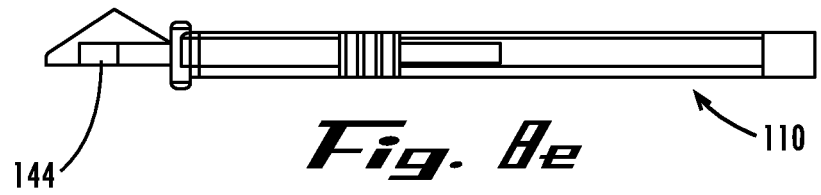
Figure 8F:
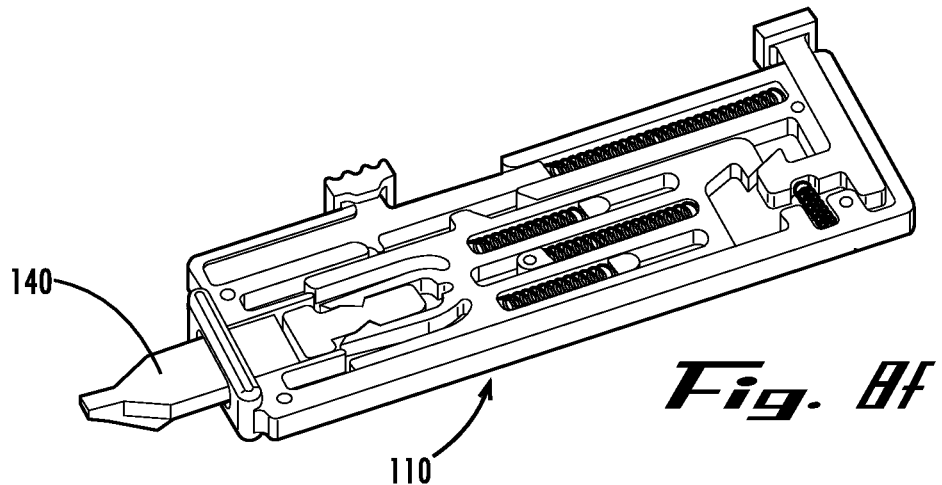
Figure 8G:
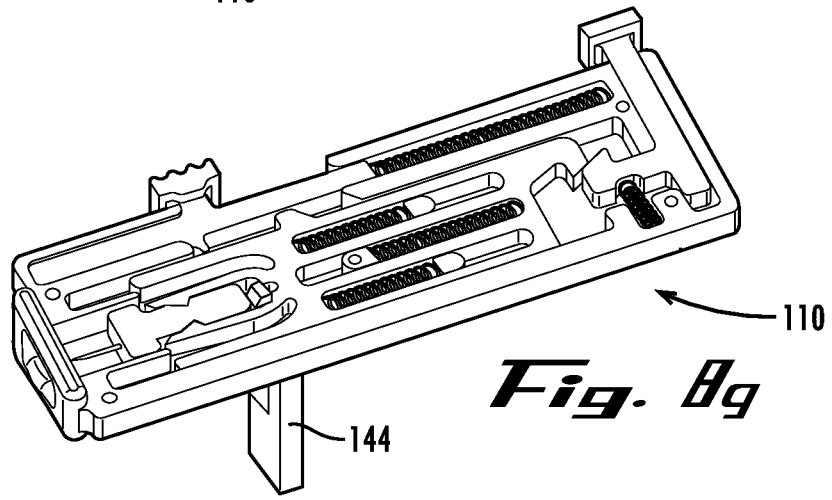
Figure 8H:
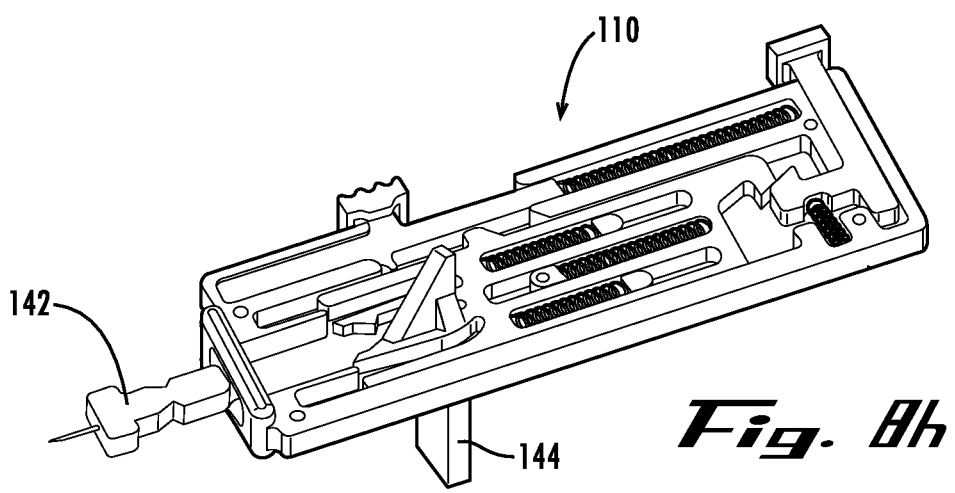
Figure 9A:
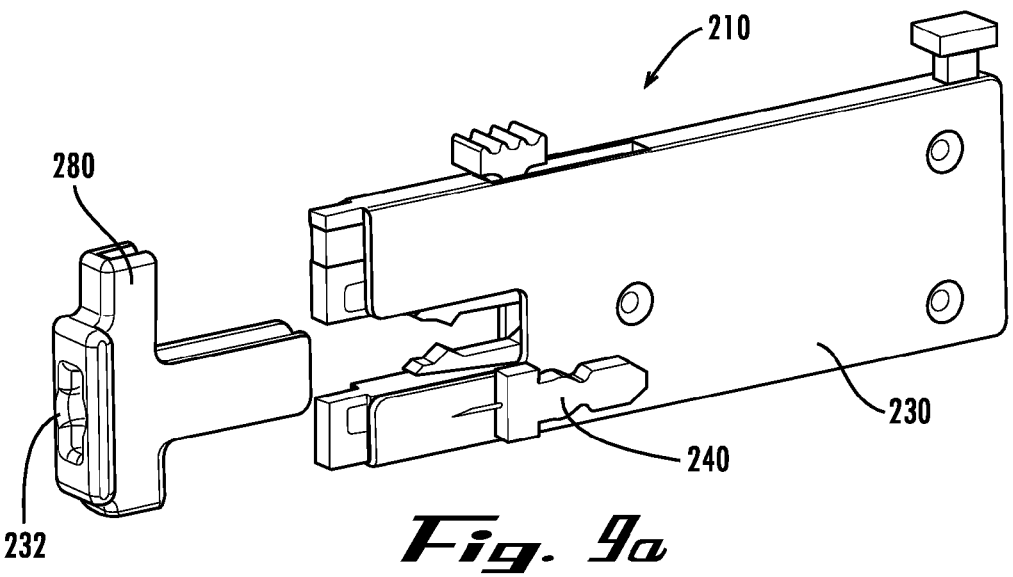
FIGS. 9a-9e show a lancing device according to another embodiment of the present invention.
Figure 9B:
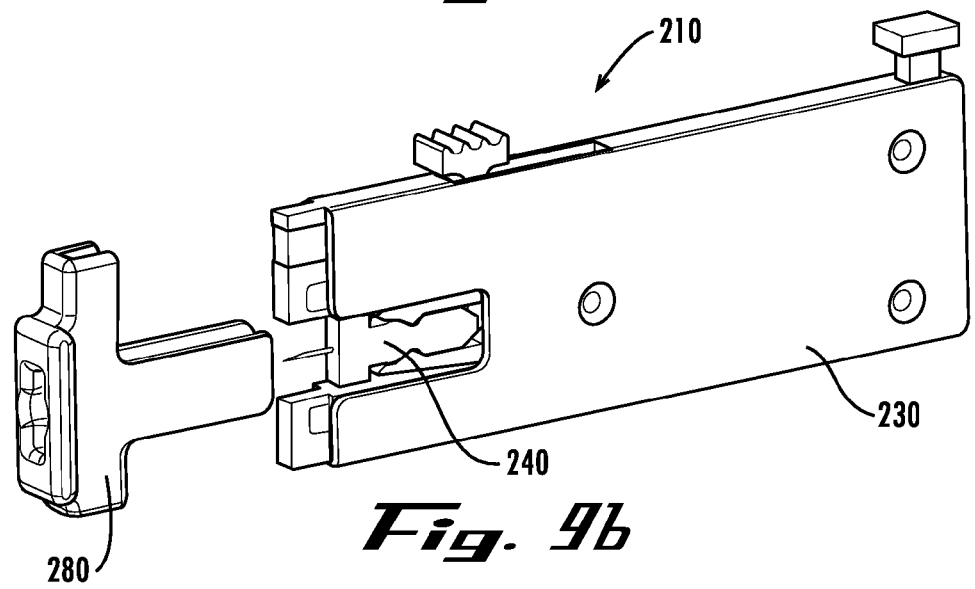
Figure 9C:
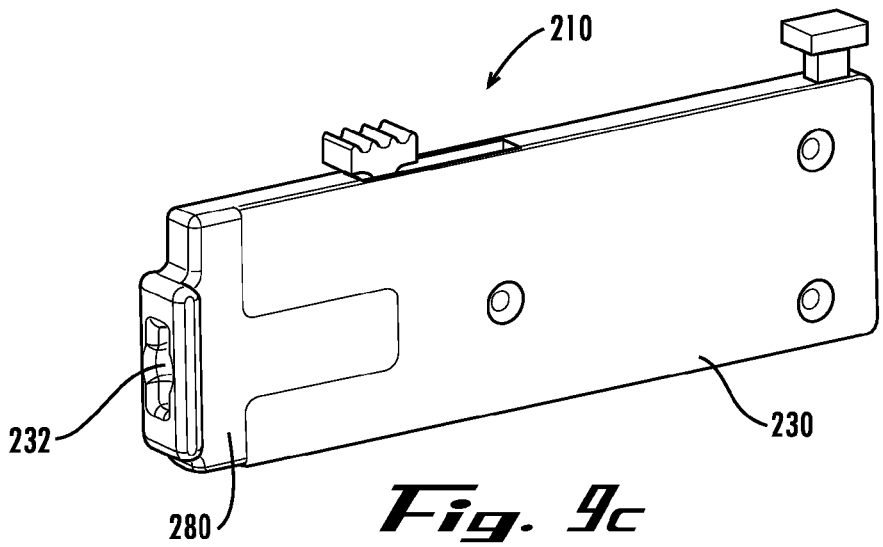
Figure 9D:
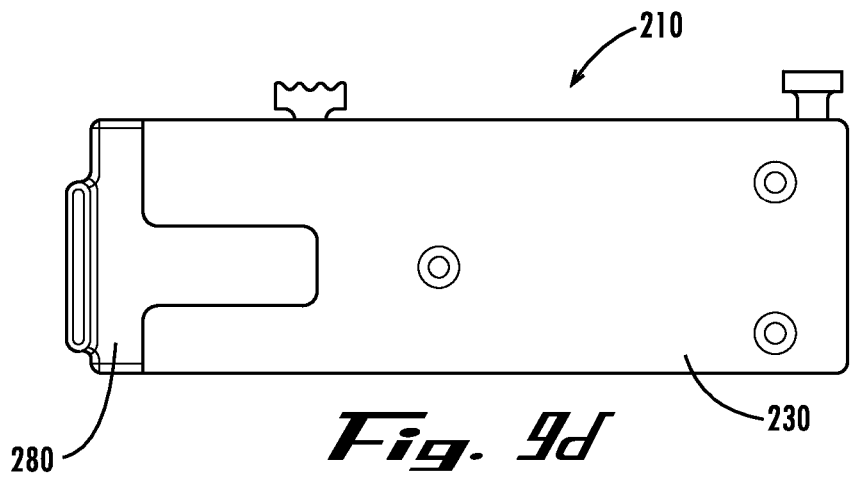
Figure 9E:
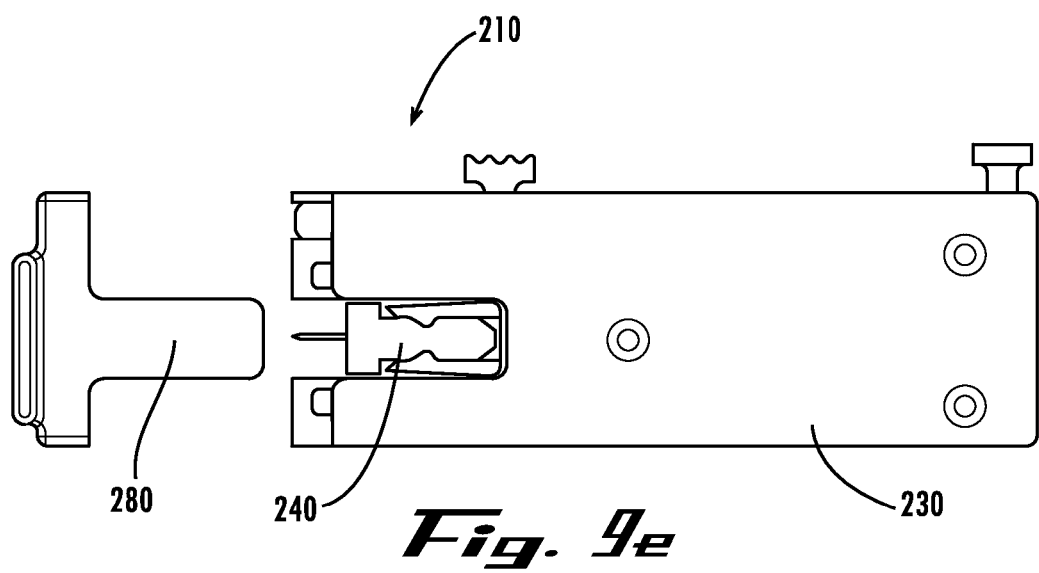
Figure 10A:
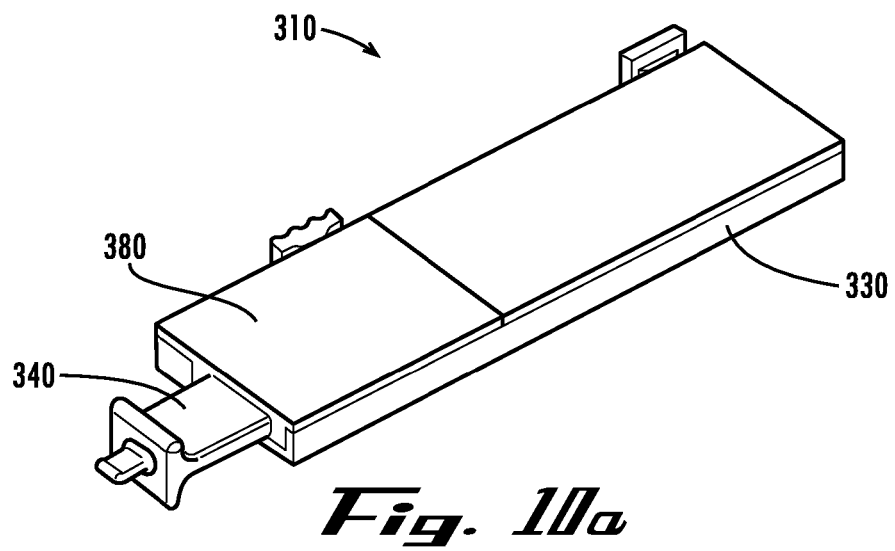
FIGS. 10a-10i show a lancing device and lancet according to another embodiment of the present invention.
Figure 10B:
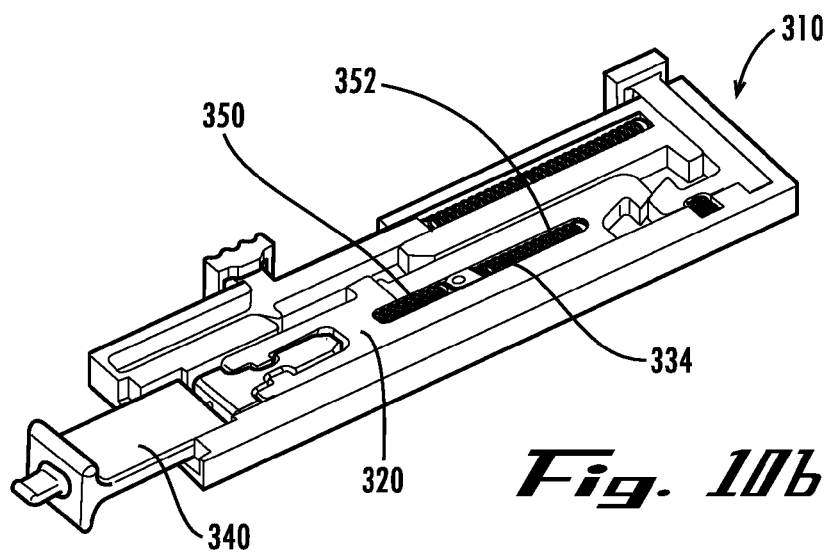
Figure 10C:
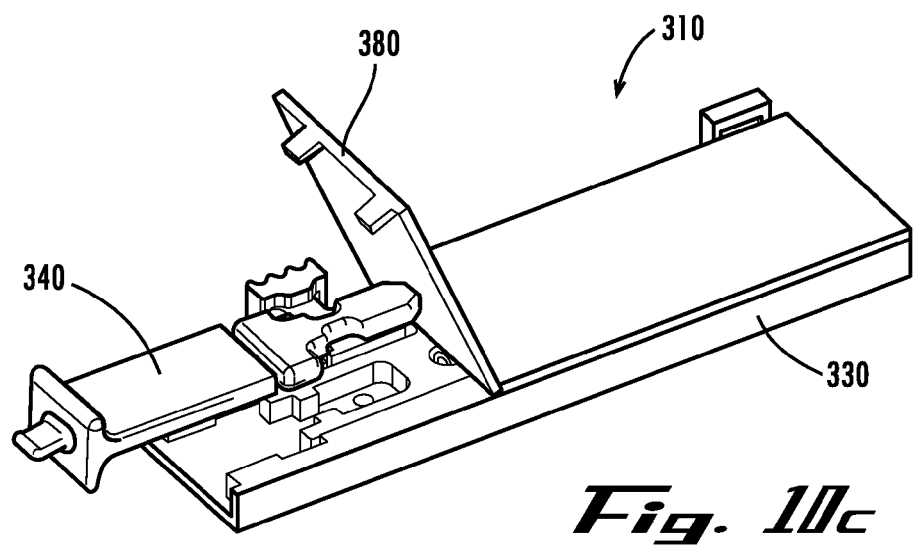
Figure 10D:
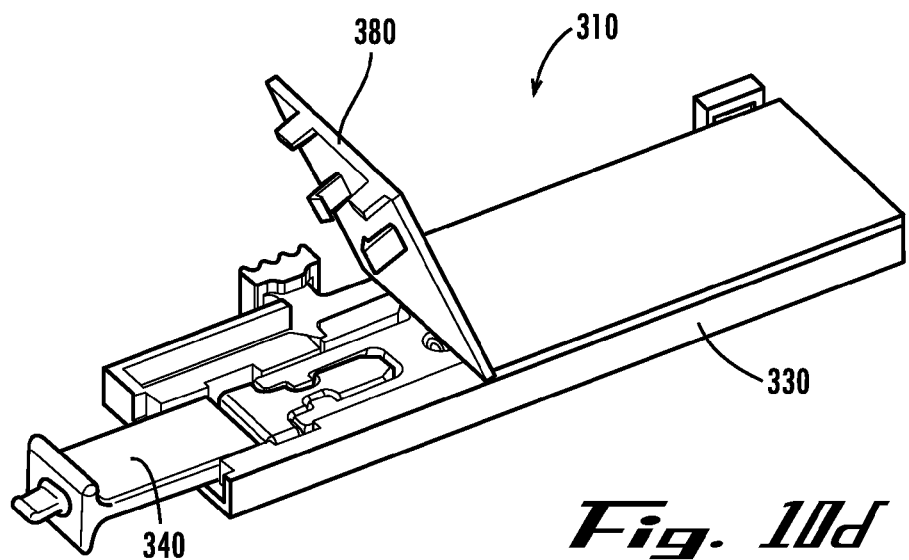
Figure 10E:
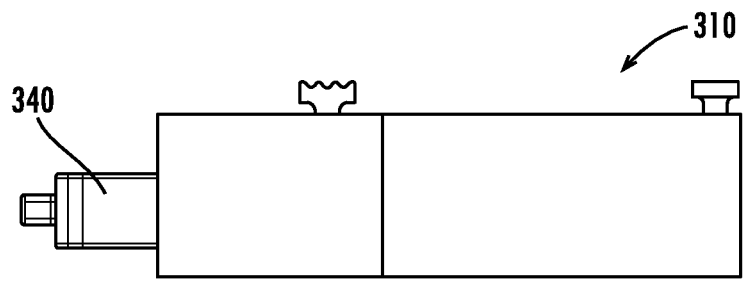
Figure 10F:
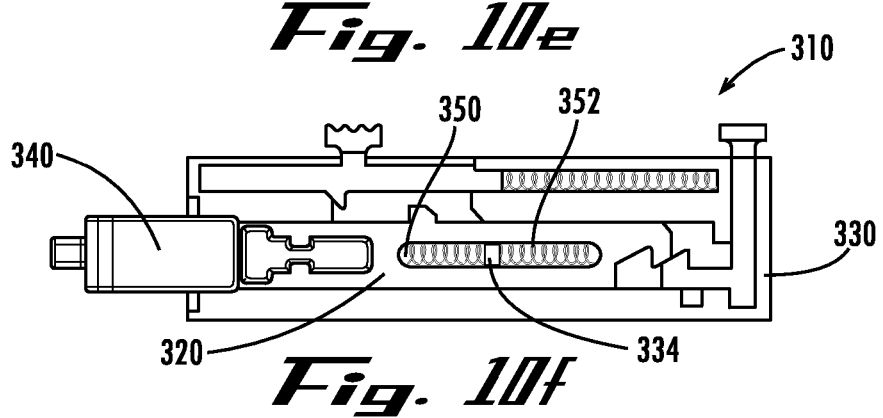
Figure 10G:
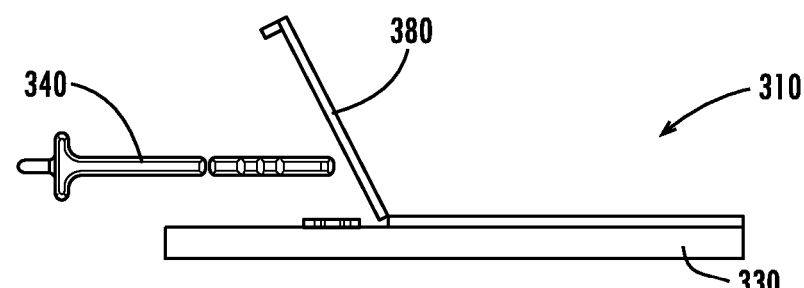
Figure 10H:
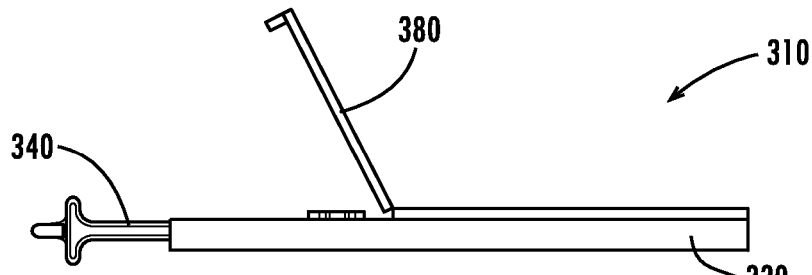
Figure 10I:
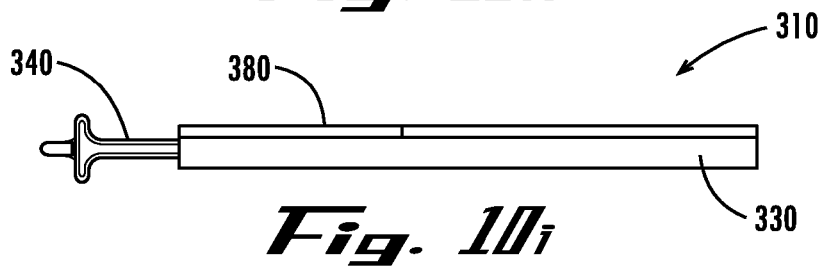
Figure 11A:
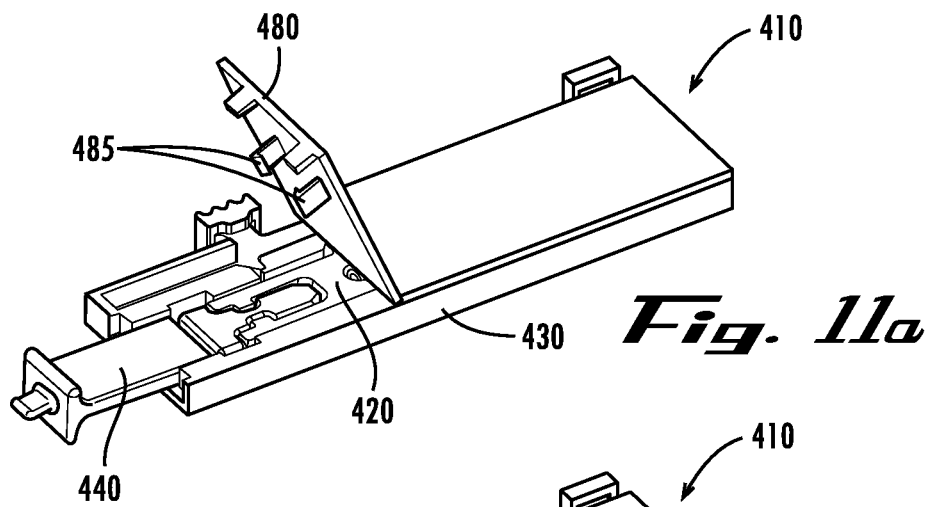
FIGS. 11a-11d show a lancing device according to another embodiment of the present invention.
Figure 11B:
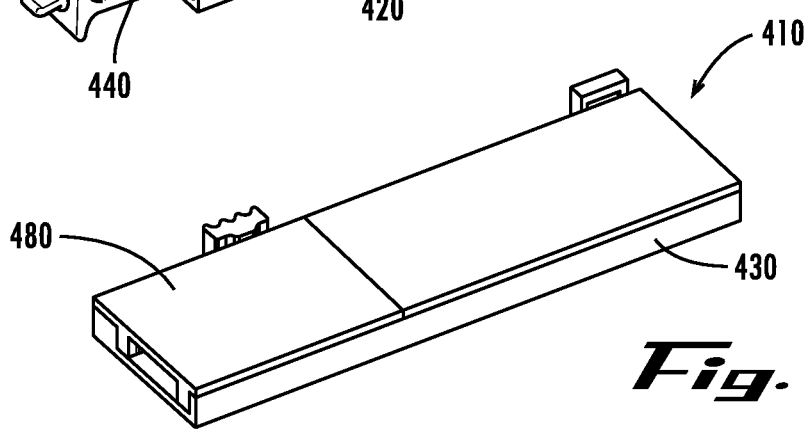
Figure 11C:
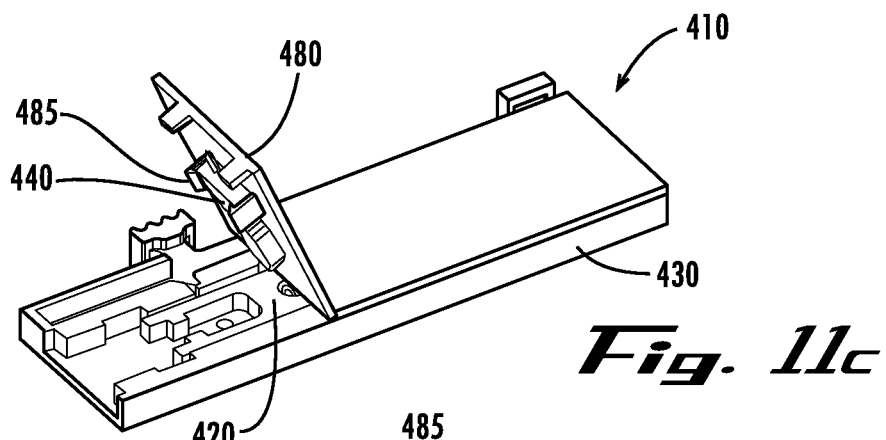
Figure 11D:
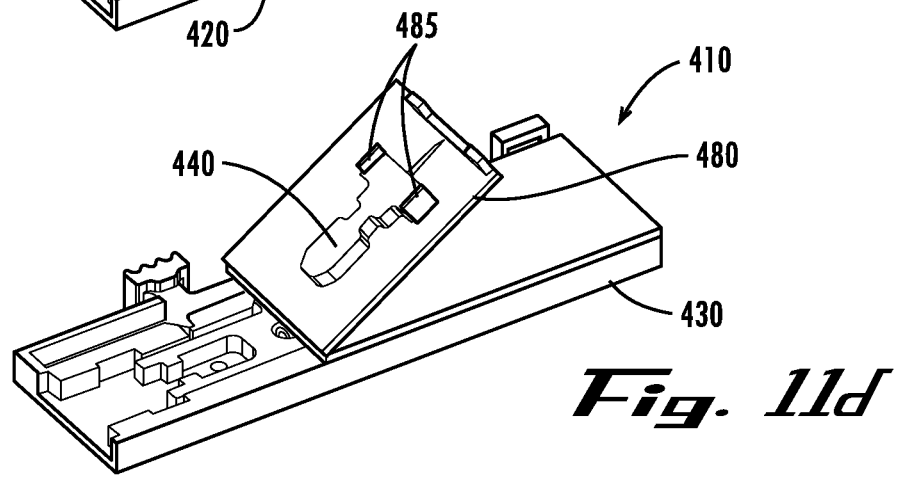

The sterility cap 44 is removed, and the slotted proximal face of the housing is placed against the subject's skin at the intended lancing site. The user presses the release button 72 of the release member 70, releasing the sear 76 from engagement with the lancet carrier 20. The lancet carrier 20 is propelled forward into its advanced position under the influence of the drive springs 50, driving the sharp lancet tip through the slotted opening 32 and outwardly of the housing 30, to penetrate the subject's skin at the lancing site (FIG. 5). The lancet carrier 20 is then retracted under the influence of the retraction spring 52, to return the lancet tip into a shielded equilibrium position within the housing (FIG. 6).

After use, the lancet body 42 is preferably removed from the lancing device 10, for replacement with a fresh lancet for subsequent use. The release finger 46 of the sterility cap 44 is inserted into a hole 39 in the housing, extending between the forks 22 of the lancet carrier, and behind the lancet body 42 (FIG. 6). The lancet carrier 20 is then retracted out of engagement with the lancet body 42 by sliding the energizing member 60 rearwardly, causing the forks 22 to flex outwardly and release the lancet body, and the used lancet is discharged from the slotted opening 32 or otherwise removed from the device 10. In alternate forms, an integral removal member is provided for releasing the lancet from the carrier, for example comprising an internal finger selectively positionable between the forks 22 of the lancet carrier and behind the lancet body 42, and an external actuation button or lever.

One or more guides or limit members 28 are optionally provided on the lancet carrier 20, moving within one or more corresponding guide channels formed in the housing 30, to maintain transverse alignment of the lancet carrier (i.e., limiting up-and-down movement of the carrier and lancet perpendicular to the lancet stroke), and to provide a forward stop to limit the stroke of the lancet in the forward axial direction thereby more precisely controlling the depth of penetration of the lancet into the skin. The forks 22 of the lancet carrier 20 are preferably guided between a pair of retaining panels 35 at the proximal end of the housing adjacent the slotted opening 32 as the lancet carrier 20 moves into its advanced or lancing position, preventing the forks from spreading apart and potentially releasing the lancet 40 during the lancing operation (FIG. 5) and providing additional transverse guidance and stability. The retaining panels do not extend so far distally, however, as to interfere with the forks 22 spreading apart to receive or release the lancet 40 when the carrier 20 is positioned in its retracted or equilibrium positions. In preferred form, the lancet body 42 is of substantially the same thickness as the lancet carrier 20, and the lancet body and the lancet carrier are coplanarly aligned when the lancet is installed, so that lateral guidance (i.e., limiting side-to-side movement of the carrier and lancet perpendicular to the lancet stroke) and stability are provided to both the lancet and the carrier during the lancing stroke as a result of smoothly-sliding, low-friction, close interaction of the parts along the interior faces of the side panels of the housing 30. By utilizing the interior faces of the housing as lateral guidance features in this manner, the need for separate lateral guidance components is eliminated and a more compact and narrow profile is enabled (FIG. 7).

FIGS. 8a-8h show another example embodiment of a lancing device 110 and a lancet 140 according to the present invention. In this embodiment, the endcap 144 of the lancet 140 comprises an inclined or curved removal surface 145, which acts as a wedge or cam when pushed into the lancet-removal opening 139, to release the lancet body 142 from the forks of the lancet carrier. Viewed from its end, the endcap 144 of the lancet 140 preferably has a generally T-shaped profile, with the removal surface 145 being positioned on the free end of its upright, and the lancet-removal opening 139 is preferably correspondingly T-shaped. In alternate embodiments, the endcap of the lancet comprises a wedge or pin, which is inserted through the lancet-removal opening 139, and the endcap is pivotally toggled to pry the spent lancet body from out of engagement with the forks of the lancet carrier.

Another example embodiment of a lancing device 210 according to the present invention is shown in FIGS. 9a-9e. In this embodiment, a detachable endcap 280 is provided at the proximal end of the housing 230. The endcap 280 is removed for access to insert a fresh lancet 240 into engagement with the lancet carrier, and/or to remove a spent lancet. The endcap 280 preferably comprises a proximal portion having a contact face defining the lancet opening 232, and at least one side panel portion extending distally therefrom to cover a cutout access portion of the housing 230 permitting lancet removal and insertion. The detachable endcap may be entirely removable from the remainder of the housing, or may be tethered or hingedly connected to the remainder of the housing to prevent loss.

In the example embodiment of the present invention depicted in FIGS. 10a-10i, the lancing device 310 comprises a housing 330 having a hinged access panel or door 380 providing access for removal and/or insertion of the lancet 340 to/from the lancet carrier 320. Additionally, a drive spring 350 and a return spring 352 are positioned within a single elongate slot formed in the lancet carrier 320, and are aligned coaxially with one another on opposite sides of a biasing lug 334 of the housing 330. This aligned spring configuration enables a housing geometry that is shorter in height than the parallel spring arrangement described above.

Another example embodiment of a lancing device 410 having a hinged access door 480 in the housing 430 is shown in FIGS. 11a-11d. In this embodiment, the inner face of the door 480 includes one or more clips 485 for retaining the lancet 440. A lancet 440 is installed into the device by placing the lancet body into the carrier 420 (FIG. 11A), or alternatively by engaging the lancet body with the clips 485 on the access door 480. The access door 480 is closed, and the device is operated in similar fashion to that described above. After use, removal of the spent lancet 440 is facilitated by the retention of the lancet on the access door 480 by the clips 485, such that the lancet may be more easily removed when the door is opened. The clips 485 optionally also provide lancet guidance.

Figure 12:
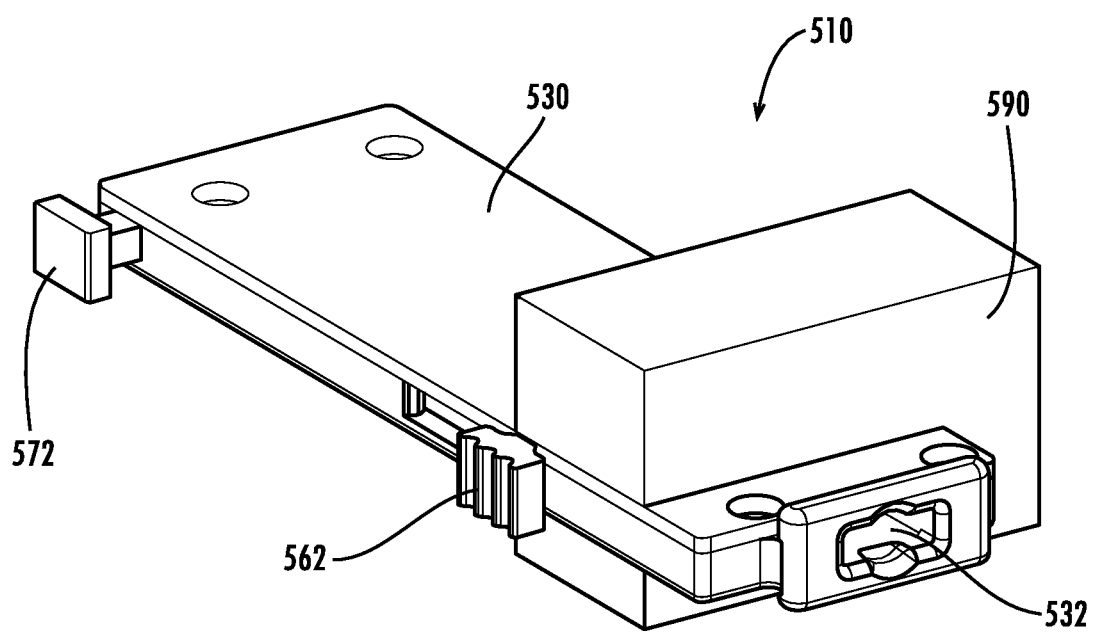
FIG. 12 shows a lancing device according to another embodiment of the present invention.
Figure 14A:
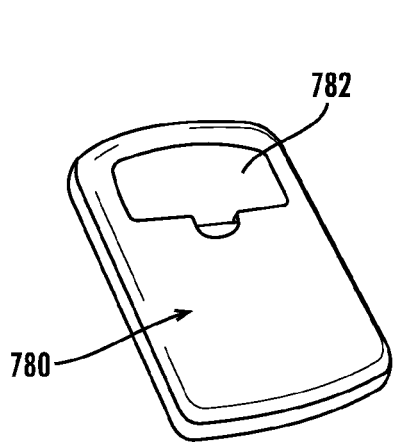
FIGS. 14a-14f show a lancing device according to another embodiment of the present invention, the lancing device being engaged onto a mounting clip installed in place of a battery cover on a blood-glucose testing meter.
Figure 14B:
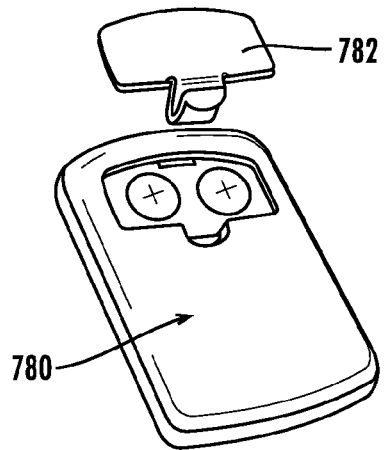
Figure 14C:
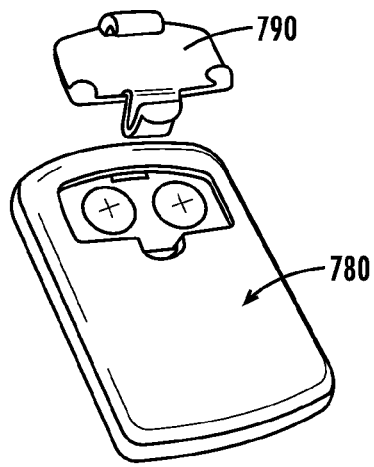
Figure 14D:
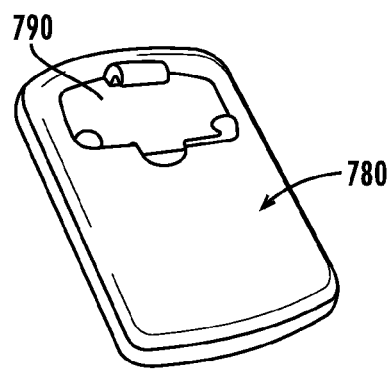
Figure 14E:
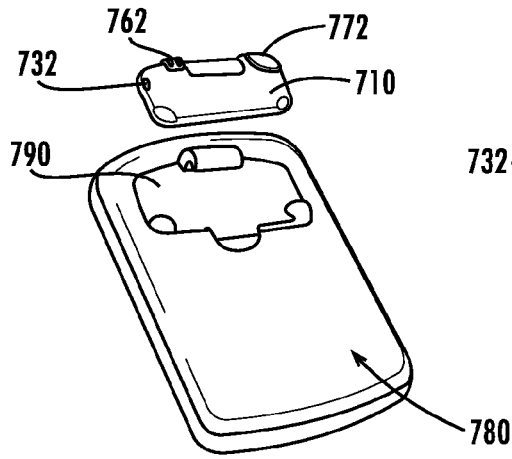
Figure 14F:
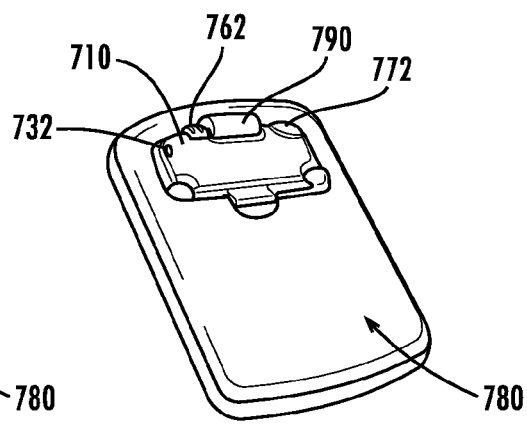

FIG. 12 shows another example embodiment of a lancing device 510 according to the present invention. In this embodiment, a clip 590 containing a plurality of lancets, preferably in a stacked or sequential array, is provided. Actuation of the energizing member 562 preferably loads a fresh lancet for use and discharges a used lancet from the lancet carrier. The clip optionally includes a collection reservoir for used lancets, or alternatively used lancets are discharged from the device for external disposal. Other than the clip-feeding lancet mechanism, the remainder of the device 510 is substantially similar to that described above, having a housing 530 containing a translational lancet carrier and drive mechanism, a lancet opening 532 through which the lancet tip projects in its extended position, a charging or energizing mechanism actuated by the energizing member 562, and a release mechanism actuated by the release button 572.

Due to the compact size and narrow profile of example embodiments, the lancing device of the present invention is suitable for mounting or attachment to a blood glucose test meter or other device or carrier. Preferably, the lancing device of the present invention is mountable on or in place of a removable portion or component of the meter, removal or alteration of which does not negatively impact the meter's operation. For example, various forms of the invention can be mounted to or in place of the removable battery cover of a blood glucose test meter, such that the lancing device is carried with the meter for greater convenience and ease of use. The lancing device can be provided as original equipment as a detachable or integral part of a new meter, and/or can be provided as an upgrade or retrofit component for backwards-compatible attachment to an existing meter, such as for example the Bayer Ascensia Contour™ blood glucose meter sold by Bayer Healthcare LLC of Mishawaka, Ind.; the BD Logic Meter; the Lifescan OneTouch Ultra Meter, and/or the Abbott FreeStyle Flash Meter. The housing of the lancing device is preferably similar in size and shape to the battery cover of the particular blood-glucose testing meter to which it is intended to be mounted, and the narrow profile of the lancing device does not significantly alter the overall external geometry of the meter. The housing of the lancing device preferably comprises external surface features substantially conforming to the attachment clips, channels, tabs, slots and/or other corresponding coupling members of a battery cover, whereby the lancing device can be snapped or clipped onto a meter in place of the standard battery cover. Preferably, one or more of the actuator components and/or the lancet opening of the lancing device project beyond or adjacent the outer peripheral edges of the meter or other object to which the device is mounted, for easier access during use.

For example, as shown in FIGS. 13a-13e, the lancing device 610 is configured for attachment in place of a battery cover 682 of a blood glucose testing meter 680. The blood glucose testing meter 680 is preferably of standard form, having a slot 684 for receiving a test strip, a display 686, and one or more controls 688. The external geometry of the lancing device 610 generally matches the shape and size of the battery cover 682, and includes one or more coupling member(s) for coupling to the meter 680 substantially similar to the corresponding coupling member(s) of the battery cover. The lancet opening 632 preferably projects a small distance beyond the side edge of the meter, such that the user can readily place a finger or alternate lancing site against the contact face surrounding the lancet opening. And the energizing member 662 and release button 672 preferably also project a small distance beyond the outer periphery of the meter, for ease of access and use.

In an another example form of the present invention shown in FIGS. 14a-14f, the lancing device 710 is mountable into or onto a mounting clip 790 that replaces the standard battery cover 782 of a test meter 780. The mounting clip preferably has a geometry and coupling member configuration substantially similar to the original battery cover, and includes one or more fingers, fittings or other retention means for engaging cooperative elements of the lancing device 710 to permanently or removably secure the lancing device thereto. The lancet opening 732, the energizing member 762, and/or the release button 772 preferably project a distance beyond the back panel of the meter, for ease of access and use.

In other embodiments, the lancing device of the present invention is integrally formed with or mountable onto a meter elsewhere other than the battery cover, as by integral molding, adhesive attachment, snap-fitting connection or other attachment means. In further alternate embodiments, the lancing device of the present invention is integrally formed with or mountable onto a carrier other than a blood glucose meter. For example, the lancing device can comprise a clip allowing it to be mounted or attached onto a purse, belt or other item, similar to a pen, a tie-clip or a small pager. Alternatively or additionally, the lancing device includes a ring or loop for attachment to a key-ring or other object, in similar fashion to a key-fob.

While the invention has been described with reference to preferred and example embodiments, it will be understood by those skilled in the art that a variety of modifications, additions and deletions are within the scope of the invention, as defined by the following claims.

What is claimed is:

1. In combination, a blood glucose testing meter comprising a battery compartment, the battery compartment comprising a chamber within the meter for housing at least one battery, and an access opening for direct insertion and removal of the at least one battery to and from the chamber through the access opening; and
   a lancing device for releasable coupling to the blood glucose testing meter over the battery compartment, wherein the lancing device takes the place of a battery cover on the blood glucose testing meter, and is repositionable relative to the blood glucose testing meter between a closed configuration wherein the lancing device covers the access opening and prevents insertion and removal of the at least one battery to and from the chamber of the blood glucose testing meter, and an open configuration wherein the lancing device does not cover the access opening and permits insertion and removal of the at least one battery to and from the chamber of the blood glucose testing meter.

2. The combination of claim 1, wherein the lancing device releasably couples directly to the testing meter over the battery compartment.

3. The combination of claim 1, wherein the lancing device is mounted to a mounting clip releasably coupled to the testing meter over the battery compartment.

4. The combination of claim 1, wherein the lancing device comprises a housing and a lancet opening disposed at one end of the housing.

5. The combination of claim 4, wherein the lancet opening of the lancing device projects at least adjacent to an outer peripheral edge of the testing meter.

6. The combination of claim 4, wherein the housing of the lancing device comprises external coupling members corresponding to those of an original battery cover of the testing meter.

7. The combination of claim 1, wherein the lancing device comprises an energizing member for charging the lancing device and a release button for activating a lancet within the lancing device.

8. The combination of claim 7, wherein the energizing member and the release button on the lancing device projects at least adjacent to an outer peripheral edge of the glucose test meter.

9. The combination of claim 1, wherein the lancing device is used in place of an original battery cover of the testing meter, the original battery cover being removed and replaced by the lancing device to cover the battery compartment, wherein the lancing device generally matches the shape and size of the battery cover.

10. The combination of claim 9, wherein the lancing device comprises at least one coupling member for coupling the lancing device to the testing meter.

11. The combination of claim 1, wherein the blood glucose testing meter includes a slot for receiving a test strip.

12. In combination, a body fluid testing meter comprising a battery compartment, the battery compartment comprising a chamber within the meter for housing at least one battery, and an access opening for direct insertion and removal of the at least one battery to and from the chamber;
    a mounting clip for releasable coupling to said battery compartment of said body fluid testing meter, wherein the mounting clip removably covers the access opening and takes the place of a battery cover of the body fluid testing meter; and
    a lancing device that is mountable to the mounting clip to at least partially overlie the battery compartment of said body fluid testing meter when the mounting clip is coupled to the body fluid testing meter, and to allow access to the battery compartment when the mounting clip is removed from the body fluid testing meter.

13. The combination of claim 12, wherein the mounting clip has a geometry and coupling member configuration substantially conforming to an original battery cover of the body fluid testing meter, the original battery cover being removed and replaced by the mounting clip to cover the battery compartment.

14. The combination of claim 12, wherein the mounting clip includes at least one retention feature for engaging cooperative elements of the lancing device to secure the lancing device thereto.

15. The combination of claim 12, wherein the lancing device includes a lancet opening for partially allowing the passage of a lancet therethrough, an energizing member for charging the lancing device, and a release button for activating a lancet within the lancing device.

16. The combination of claim 15, wherein at least one of the lancet opening, energizing member, and the release button project a distance beyond a back panel of the testing meter.

17. The combination of claim 12, wherein the body fluid testing meter comprises a slot for receiving a test strip.

18. A testing meter comprising:
    a housing defining a slot therein for receiving test media;
    a display for outputting test results, the display being exposed and visible from external of the housing;
    a battery compartment for receiving a battery, the battery compartment comprising a chamber within the meter for housing at least one battery, and an access opening for direct insertion and removal of the at least one battery to and from the chamber; and
    a lancing device for coupling to the housing over the battery compartment, wherein the lancing device is movable relative to the testing meter between an open position allowing insertion and removal of the at least one battery to and from the chamber and a closed position preventing insertion and removal of the at least one battery to and from the chamber.

19. The testing meter of claim 18, wherein the lancing device is movable from a first position covering the battery compartment to a second position allowing access to the battery compartment.

20. The testing meter of claim 18, wherein the lancing device is detachably secured to the housing by at least one releasable coupling.

21. The testing meter of claim 18, wherein the lancing device comprises a lancet opening positioned at least flush with a side edge of the meter housing when the lancing device is coupled to the housing over the battery compartment.

22. The testing meter of claim 21, wherein the lancet opening projects beyond the side edge of the meter housing when the lancing device is coupled to the housing over the battery compartment.

23. The testing meter of claim 18, wherein the lancing device couples directly to the housing.

24. The testing meter of claim 18, wherein the lancing device couples indirectly to the housing via a mounting clip.

* * * * *